(12) United States Patent
Austin et al.

(10) Patent No.: US 6,827,340 B2
(45) Date of Patent: Dec. 7, 2004

(54) CPAP HUMIDIFIER

(75) Inventors: Gary Austin, Euclid, OH (US); James T. Austin, Concord Township, OH (US)

(73) Assignee: Taga Medical Technologies, Inc., Mentor, OH (US)

( * ) Notice: Subject to any disclaimer, the term of this patent is extended or adjusted under 35 U.S.C. 154(b) by 96 days.

(21) Appl. No.: 09/928,896

(22) Filed: Aug. 13, 2001

(65) Prior Publication Data

US 2002/0020930 A1 Feb. 21, 2002

Related U.S. Application Data

(60) Provisional application No. 60/225,171, filed on Aug. 14, 2000.

(51) Int. Cl.⁷ ............................ B01F 3/04; A61M 15/00
(52) U.S. Cl. ................................. 261/119.1; 128/204.14
(58) Field of Search ............................... 261/119.1, 123, 261/125; 128/203.16, 203.17, 204.14

(56) References Cited

U.S. PATENT DOCUMENTS

| 151,153 | A | * | 5/1874 | Palmer |
| 283,025 | A | * | 8/1883 | Rowan |
| 415,646 | A | * | 11/1889 | Kusnezov |
| 453,806 | A | * | 6/1891 | Grutzner et al. |
| 716,380 | A | * | 12/1902 | Clawson |
| 1,035,954 | A | | 8/1912 | Eklund et al. |
| 2,445,347 | A | | 7/1948 | Ehlinger |
| 2,608,399 | A | * | 8/1952 | Alcock |
| 2,612,745 | A | * | 10/1952 | Vecchio |
| 3,265,067 | A | * | 8/1966 | Ehlinger |
| 4,112,939 | A | | 9/1978 | Visconti |
| 4,367,734 | A | | 1/1983 | Benthin |
| 4,430,994 | A | * | 2/1984 | Clawson et al. |
| 4,621,632 | A | * | 11/1986 | Bartels et al. |
| 4,861,523 | A | * | 8/1989 | Beran |
| 5,231,979 | A | | 8/1993 | Rose et al. |
| 5,537,997 | A | | 7/1996 | Mechlenburg et al. |
| 5,564,415 | A | | 10/1996 | Dobson et al. |
| 5,598,837 | A | | 2/1997 | Sirianne, Jr. et al. |
| 5,655,522 | A | | 8/1997 | Mechlenberg et al. |
| 5,673,687 | A | | 10/1997 | Dobson et al. |
| 5,916,493 | A | | 6/1999 | Miller |
| 6,010,118 | A | | 1/2000 | Milewicz |
| 6,095,505 | A | | 8/2000 | Miller |
| 6,135,432 | A | * | 10/2000 | Hebblewhite et al. |
| 2002/0020930 | A1 | * | 2/2002 | Austin et al. |

OTHER PUBLICATIONS

Respironics, Inc., "Sleep Disorders—Oasis Humidifier", Mar. 2000.
Kline, Lewis R., MD, "Breathing Easier", Advance for Managers of Respiratory Care, Apr. 2000, pp. 48, 50 and 51.

* cited by examiner

Primary Examiner—Scott Bushey
(74) Attorney, Agent, or Firm—Pearne & Gordon LLP

(57) ABSTRACT

Passive humidifier for a continuous positive airway pressure (CPAP) device having a plurality of chambers defined by arced baffles. Each opening between the arced baffles is provided with a deflector baffle to prevent direct passage of air.

10 Claims, 7 Drawing Sheets

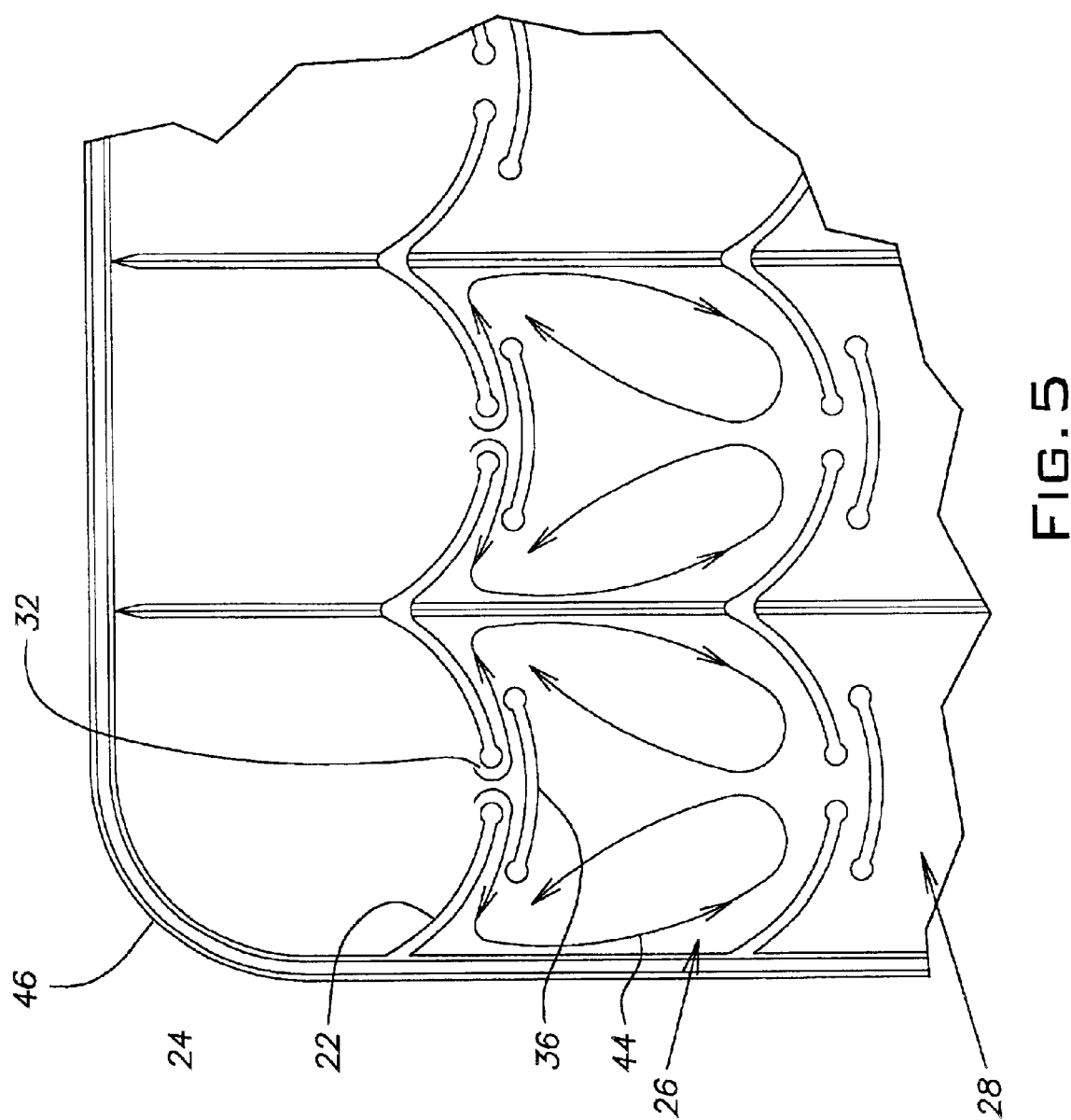

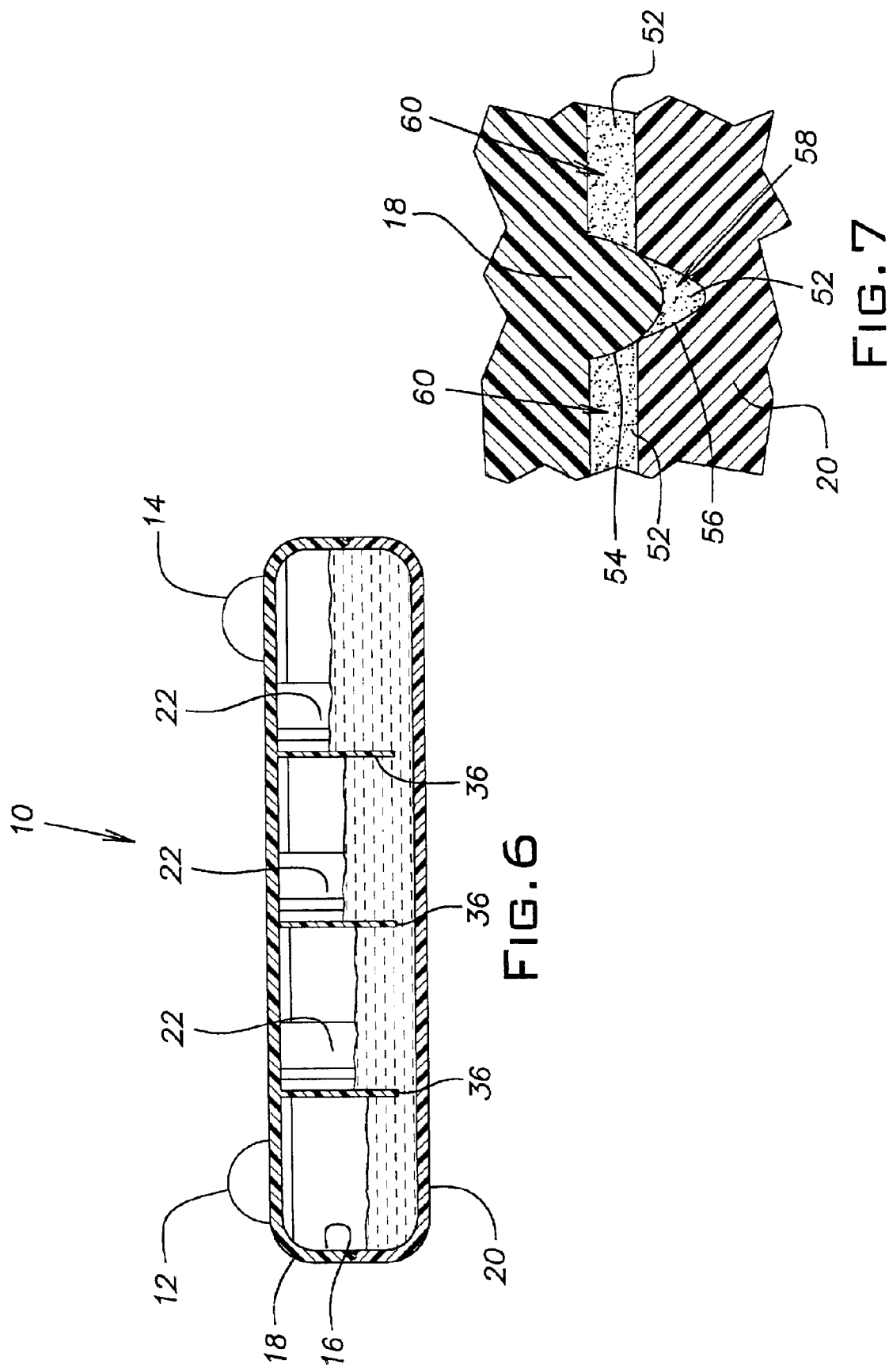

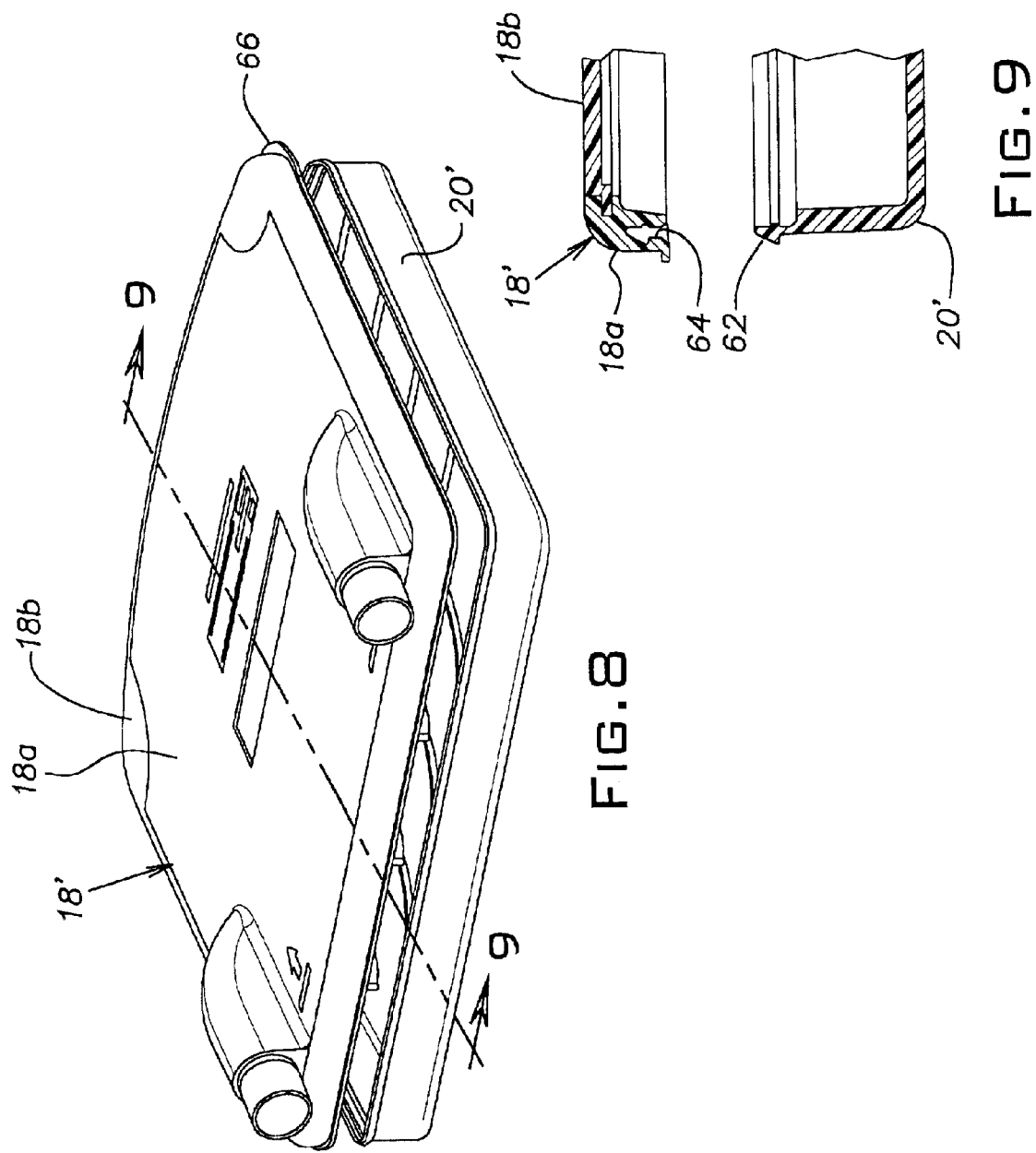

CPAP HUMIDIFIER

CROSS-REFERENCE TO RELATED APPLICATION

This application claims the benefit of U.S. Provisional Patent Application Ser. No. 60/225,171 filed on Aug. 14, 2000 now abandoned.

BACKGROUND OF THE INVENTION

1. Field of the Invention

The present invention relates generally to a passive humidification apparatus, and more specifically to a humidifier for a continuous positive airway pressure (CPAP) device.

2. Relevant Prior Art

CPAP devices are now commonly used to treat a variety of respiratory disorders, including sleep apnea. CPAP devices normally consist of an air pump connected to a mask worn by a patient while they are sleeping.

Although CPAP devices have been very successful in treating these disorders, there is at least one associated drawback. The air that is introduced into the patient's respiratory system tends to have the effect of drying out mucous membranes. In order to mitigate this problem, several types of passive humidifiers have been developed that can be connected between the CPAP device and the associated mask without interfering with the normal operation of the device.

One such passive humidifier is disclosed in U.S. Pat. No. 5,231,979 to Rose et al. This humidifier consists mainly of a chamber having an inlet and an outlet and that is partially filled with water. In operation, the outlet of a CPAP device is connected to the inlet of the humidifier and the mask is connected to the outlet of the humidifier. When the air supplied by the CPAP device enters the humidifier chamber and passes over and contacts the water, some moisture is added to the air through evaporation before the air ultimately passes to the mask and into the patient. This humidifier, however, is very ineffective and normally produces insufficient levels of humidity.

To improve the efficacy of the passive humidification system, some such humidifiers have been provided with baffles located within the humidifier chamber. One such baffled humidifier is disclosed in U.S. Pat. No. 5,598,837 to Sirianne, Jr. et al. In this humidifier, air is made to flow around the baffles which increases its length of contact with the water and also tends to augment the evaporation process. However, this humidifier design still falls short of providing an optimum level of moisture in the output air. Additionally, the shape of this humidifier precludes most CPAP devices from resting on top of the humidifier, and thus it significantly increases the footprint of the CPAP system.

BRIEF SUMMARY OF THE INVENTION

According to one aspect of the present invention, a humidifier for a continuous positive airway pressure device is provided. The humidifier comprises a humidifier body, an air inlet provided to the humidifier body, an air outlet provided to the humidifier body, and a plurality of chambers defined within the humidifier body. The humidifier further comprises a plurality of baffles between one of the plurality of chambers and an adjacent one of the plurality of chambers, an opening provided between two of the plurality of baffles, the opening connecting the adjacent two of said plurality of chambers, and a deflector baffle being one of the plurality of baffles, the deflector baffle being located proximate to the opening and defining a serpentine fluid flow path between the adjacent chambers.

According to another aspect of the present invention, a humidifier comprises a non-planar dividing wall separating an adjacent two of said plurality of chambers, and an opening in the dividing wall providing fluid communication between chambers.

According to a further aspect of the present invention, a humidifier comprises a base, a cover having a resilient peripheral portion removably securing the cover to the base, a chamber defined by the base and cover, an inlet in communication with the chamber, and an outlet in communication with the chamber.

BRIEF DESCRIPTION OF THE DRAWINGS

FIG. 5 is a detail of air flow within a CPAP humidifier according to an embodiment of present invention;

FIG. 6 is a sectional view taken along section line 6—6 of the CPAP humidifier shown in FIG. 2;

FIG. 7 is a sectional detail showing a seam of the CPAP humidifier of FIG. 6;

FIG. 8 is a perspective view of a CPAP humidifier according to another embodiment of the present invention; and FIG. 9 is a sectional detail taken along section line 9—9 of the CPAP humidifier shown in FIG. 8.

DETAILED DESCRIPTION

In a passive humidification system, factors contributing to humidification include increased surface contact and decreased air pressure. By controlling these factors through humidifier design, the overall performance of the humidifier can be increased.

One way to positively affect both of these factors is by preventing laminar air flow through the system. When turbulence is introduced, the air does not travel in a straight line, and thus it will remain in the system longer and have increased surface contact with the water. Furthermore, assuming a constant input and output pressure, turbulent flow has the effect of increasing airflow velocity within the system. When the velocity of the air flowing across the surface of the water is increased, the air pressure above the water correspondingly decreases which effectively increases the rate of evaporation. Turbulent airflow can be created in several ways.

One way to create turbulence in a system is by designing the system with a high Reynolds number. As will be appreciated by one skilled in the art, the higher the Reynolds number, the greater the incidence of turbulent flow. The Reynolds number of a system is directly related to the velocity of flow. In the present humidifier design, positive pressure is placed on the air inlet, thereby increasing the velocity of the air traveling through it.

Another way to increase turbulence and air velocity is by providing baffles that redirect the airflow. Further, by constricting the airflow space, the baffles will tend to increase the Reynolds number of the system.

As will be shown below, the shape and placement of baffles in the system are critical to providing the desired effect.

Figure 1:
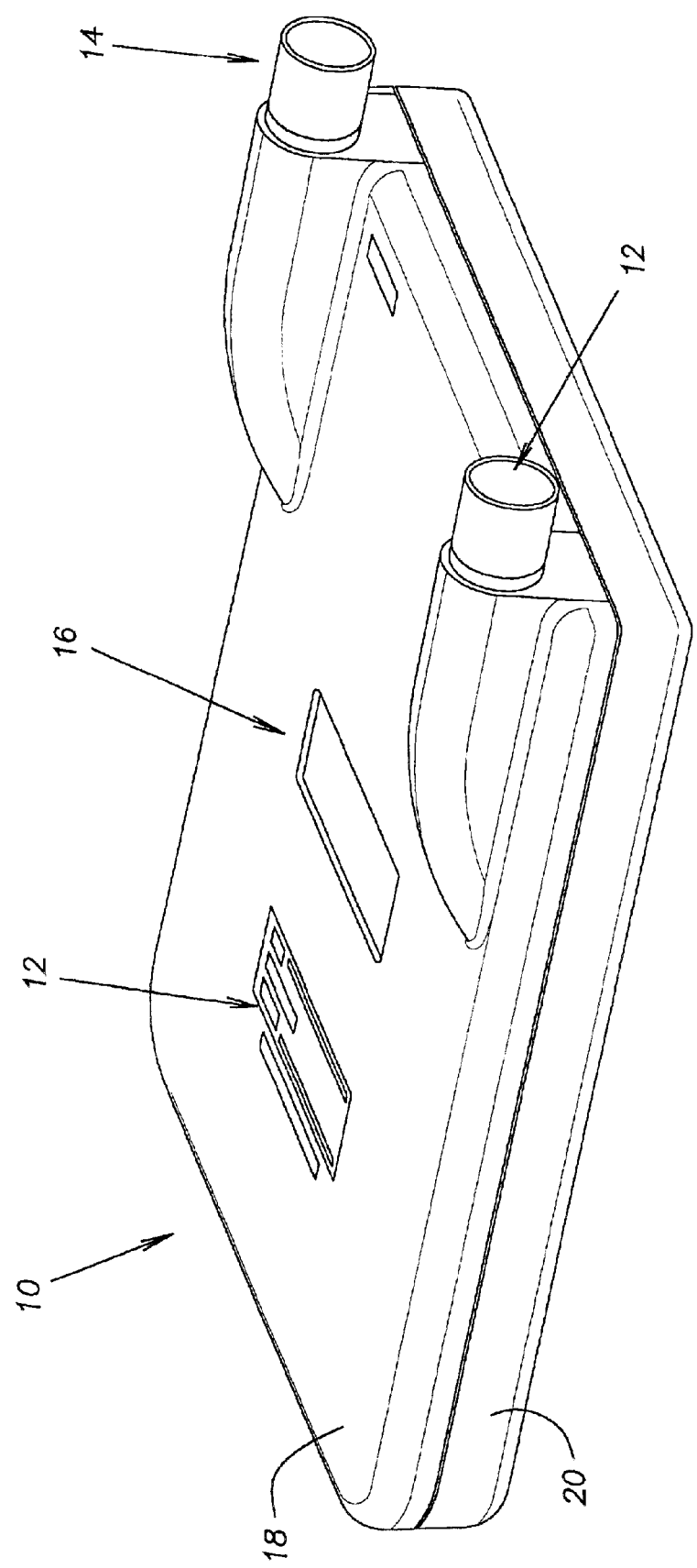
FIG. 1 is perspective view of a CPAP humidifier according to an embodiment the present invention.
Figure 2:
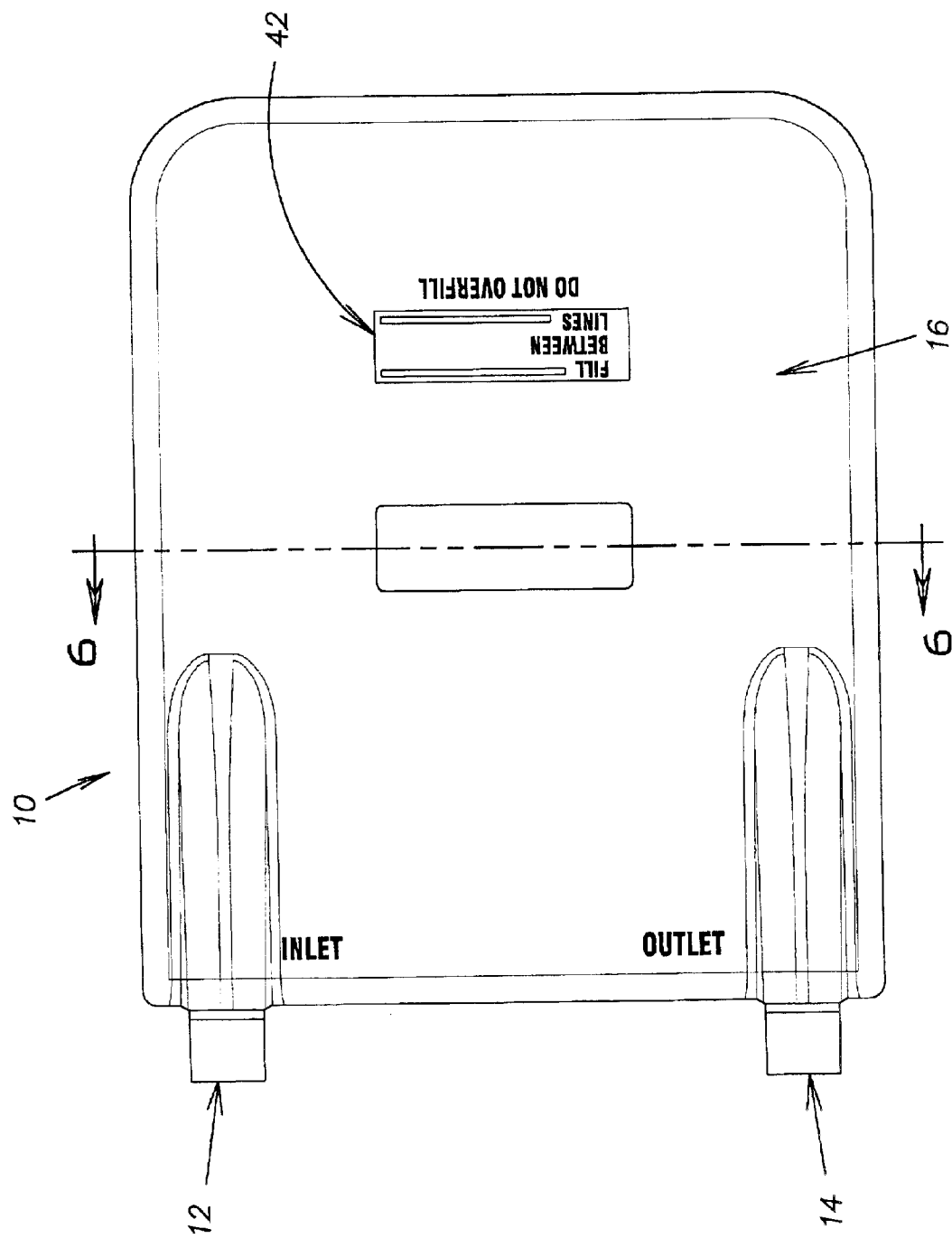
FIG. 2 is plan view of the CPAP humidifier of FIG. 1.

FIGS. 1 and 2 show the exterior of a CPAP humidifier 10 according to the present invention. The humidifier 10 is provided with an air inlet 12, an air outlet 14, and a humidifier chamber 16. In use, the inlet 12 is connected to the outlet of a CPAP device (not shown) and the outlet 14 is connected to a patient delivery device, such as a mask (not shown). Both of these connections are normally accomplished using flexible hose. As best seen in FIG. 1, the humidifier 10 comprises a cover portion 18 and a base portion 20.

Figure 3:
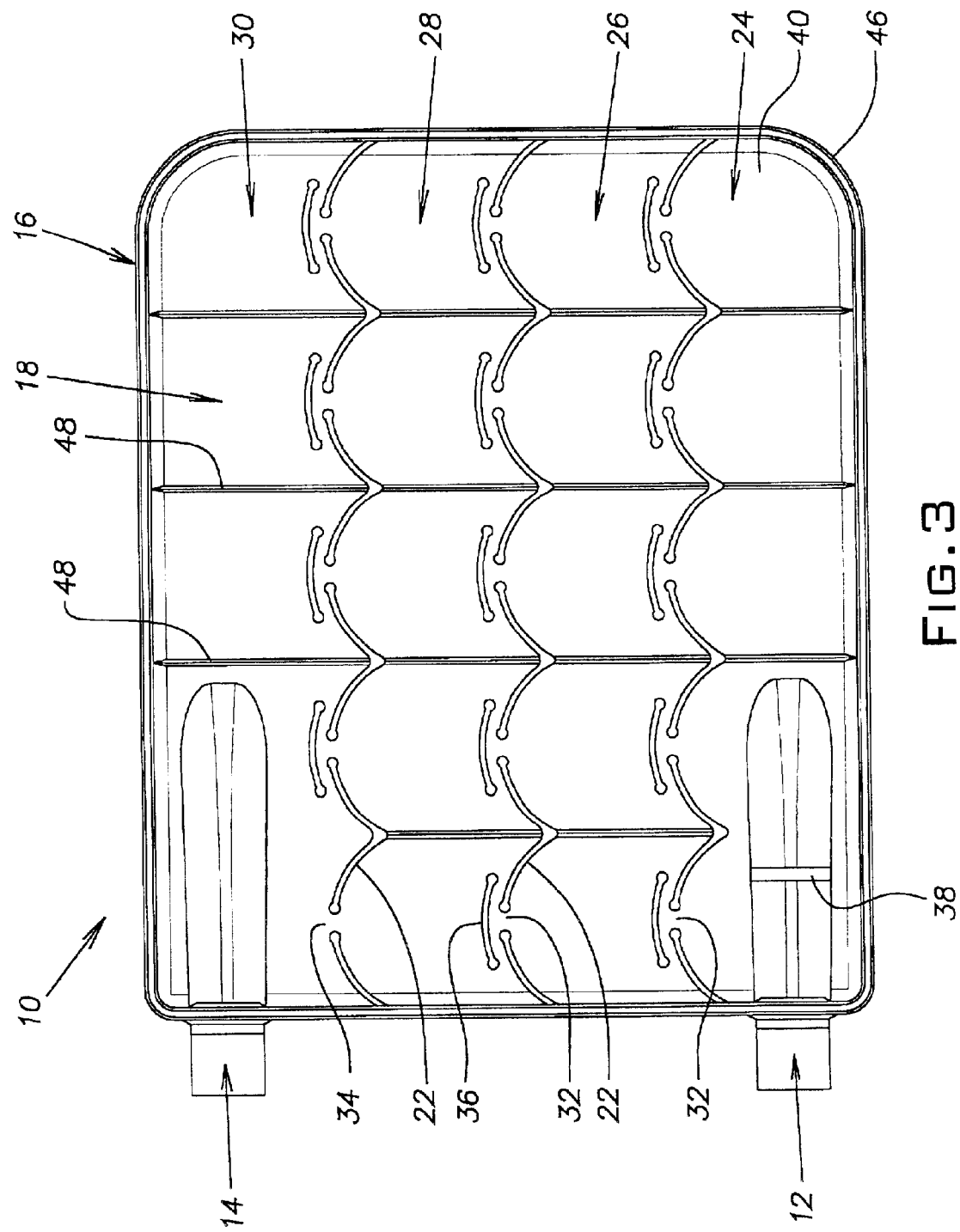
FIG. 3 is a plan view of a cover portion of the CPAP humidifier of FIG. 1.
Figure 4:
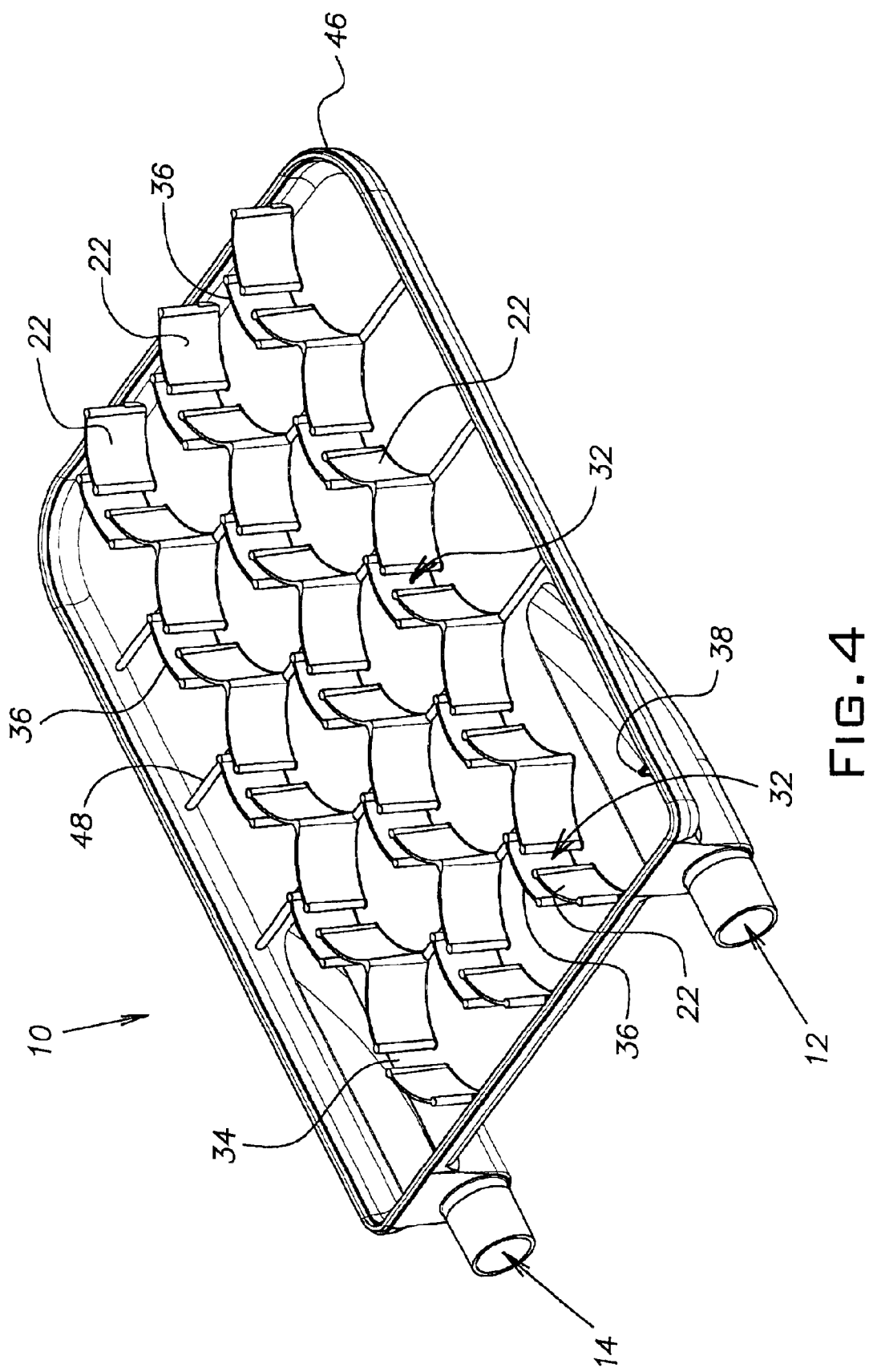
FIG. 4 is a perspective view of the cover portion of FIG. 3.

FIGS. 3-5 show the cover 18 of the humidifier 10 removed from the base 20. The cover 18 is provided with a plurality of arced baffles 22. Alternatively, the baffles 22 could be curvilinear, flat or formed from a plurality of flat portions connected at an angle.

The baffles 22 are arranged to form non-planar dividing walls so that the humidifier chamber 16 is effectively divided into four separate parallel chambers 24, 26, 28, 30. The term non-planar as used herein with reference to the dividing wall refers to a body that is made up of at least two separate components which are not coplanar with respect to one another. For example, the wall of the present embodiment comprises individual baffles 22 which are curved and/or angled with respect to one another.

The first chamber 24 is adjacent to the air inlet 12 and the second chamber 26. The second chamber 26 is also adjacent to the third chamber 28. The third chamber 28 is also adjacent to the fourth chamber 30. The fourth chamber is also adjacent to the air outlet 14.

Openings 32 are provided between adjacent baffles 22 to allow adjacent chambers 24-30 to communicate with one another. Further, the baffles 22 do not extend completely to the base 20, leaving a space connecting all of the chambers 24-30. Each of the openings 32, excluding one opening 34 that is in closest proximity to the air outlet 14, is provided with a deflector baffle 36 spaced away from the opening 32. The deflector baffle 36 is provided as part of the dividing wall and defines a serpentine flow path between two adjacent chambers. The term serpentine, as used herein, refers to a path which is not linear, having at least one bend. As an alternative, a deflector baffle could be provided at opening 34.

As an alternative, a dividing wall could be provided that is single curvilinear baffle being provided with apertures to serve as openings 32. Thus, a non-planar dividing wall according to the present invention need not comprise separate baffles wherein the space between them provides the openings 32.

Additionally, an inlet baffle 38 is provided within the air inlet 12 to direct airflow toward the far end 40 of the first chamber 24. This helps better distribute the air flow among all of the openings 32, since the air flow will naturally favor the openings 32 closest to the inlet 12.

In operation, the humidifier chamber 16 is filled through either the inlet 12 or the outlet 14 with the humidifier 10 oriented in a vertical position. As shown in FIGS. 1 and 2, the chamber 16 should be filled with water up to between a pair of fill lines 42 marked on the cover 18. The chamber 16 is made from a transparent material to allow for easy determination of the proper water level. The humidifier 10 is then placed in a horizontal position, so that the baffles 22 extend vertically.

Referring again to FIGS. 3-5, when air enters the inlet 12 it is deflected downward toward the water by the cover 18 and the inlet baffle 38. As a result of this deflection and the inertia of the air molecules, the air is distributed along the length of the first chamber 24. Continued airflow from the inlet 12 forces the air toward the first set of baffles 22 and eventually through the openings 32.

The deflectors 36 create back-pressure and prevent the air from passing to the second chamber 26 too quickly. The deflectors 36 also direct the air outward from the openings 32 and around the arced baffles 22. This air movement continues through the second chamber 26 and third chamber 28 until the air is finally pushed into the fourth chamber 30 and through the outlet 14.

As shown in FIG. 5, during the time when the air is with each chamber 24-30, a cooperation between the arced shape of the baffles 22, the position of the openings 32 and the deflection of the deflectors 36 causes the airflow to enter in an indirect serpentine fashion and circle a number of times within each chamber 24-30 before it exits through the opening 32. The indirect airflow and circling or eddying 44 causes additional turbulence, resulting in increased airflow velocity and significantly extending the duration of contact between the air and water. All of these effects taken together lead to enhanced evaporation and humidification of the air within the chamber. The curved corners 46 of the chamber 16 have a radius that matches the baffles 22 to further enhance the eddy effect.

Since the baffles 22 do not extend fully to the base 20, the water is free to flow within the chamber 16. This helps to further enhance evaporation and minimize the energy necessary to break water molecules away from the surface of the water by decreasing the effect of surface tension. Thus, as shown in FIG. 6, the direction of air flow tends to cause the water level in each successive chamber 24-30 to be higher than the previous one. For this reason, no deflector 36 is provided at opening 34, helping to prevent excess back-pressure from accumulating and causing water to be forced through the outlet 14.

Further, both the inlet 12 and the outlet 14 are raised above the top of the cover 18 to help prevent water from inadvertently flowing out of the chamber 16.

In addition to humidifier efficiency, the design of the humidifier 10 is based on some other considerations. The cover 18 is provided with lateral ribs 48 that provide help to stiffen the surface of the cover 18. This, along with the flat top design of the cover 18, allow a CPAP device to be placed on top of the humidifier to minimize the overall footprint. The ribs 48 have been strategically positioned to help trap airflow and to some degree enhance the eddying effect. Additional ribbing (not shown) is provided on the exterior surface of the base 20 to provide additional strength. This ribbing is designed to mirror the baffles 22 within the chamber 16 for purely aesthetic reasons.

As shown in FIGS. 1-2, the cover 18 can be molded from a single piece of rigid plastic and permanently secured to the base 20. As shown in FIG. 7, the cover 18 is secured to the base 20 using a permanent adhesive 52. Since many prior art devices are clamped together and sealed with a flexible gasket, they are more prone to leakage. To further prevent leakage, a tongue 54 provided on the cover 18 fits into a groove 56 provided on the base 20 and the adhesive 52 fills a void 58 between the tongue and the groove. Excess adhesive 52 flows into gaps 60 that remain between the cover 18 and the base 20.

Alternatively, as shown in FIG. 8, a removable cover 18' can be used. The removable cover 18' is formed as two-piece structure. A main cover portion 18a is formed from rigid material, like that of the one-piece cover 18. The main portion 18*a* is surrounded by a sealing cover portion 18*b* that is formed from a flexible material, such as rubber, molded around the main portion 18*a*. The flexible sealing portion 18*b* forms a sufficiently air and water tight seal with a modified base 20', but is removable from the base 20' to allow the interior surfaces of the humidifier 10 to be cleaned. The resilient nature of the sealing portion 18*b* keeps the cover 18' securely in place on the base 20'. Alternatively, the cover 18' could be constructed as a single piece.

As shown in FIGS. 9 and 10, the base 20' has a ribbed projection 62 which extends around the top edge of the base 20'. The projection 62 snaps into a corresponding recess 64 on provided in the bottom edge of the sealing portion 18*b*. A tab 66 is provided on the sealing portion 18*b* to allow the sealing portion 18*b* to be deformed by manually applied pressure, breaking the seal and allowing removal of the cover 18'.

Further, because CPAP devices generally contain electric motors, they tend to produce heat when run continuously. By placing a CPAP device on top of the humidifier chamber 16, some heat may be transferred to the water, thereby increasing the rate of evaporation.

To further enhance humidification, a separate heater (not shown) could be provided to the humidifier 10. Although heaters are well known for use with humidifiers, a heater used with the present design would adequately work at lower temperature than in prior art devices. Lower temperatures generally provide safer operation.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A humidifier for a continuous positive airway pressure device, comprising:

a humidifier body;

an air inlet provided to the humidifier body;

an air outlet provided to the humidifier body;

a plurality of chambers defined within the humidifier body;

a plurality of elongated baffles arranged in a row extending in a longitudinal direction of each of the plurality of baffles, and the row being positioned between one of the plurality of chambers and an adjacent one of the plurality of chambers;

an opening provided between two of the plurality of baffles of the row, the opening connecting the adjacent two of said plurality of chambers; and a deflector baffle located proximate to the opening and defining a serpentine fluid flow path between the adjacent chambers.

2. The humidifier of claim 1, wherein the air outlet is spaced away from the humidifier body and defines an air outlet chamber.

3. The humidifier of claim 1, wherein the air inlet is provided with an inlet baffle.

4. The humidifier of claim 1, wherein at least one of the plurality of baffles is curved.

5. The humidifier of claim 1, wherein at least one of the plurality of baffles is connected to a top side of the humidifier body and is spaced apart from a bottom side of the humidifier body.

6. The humidifier of claim 1, wherein each of the plurality of baffles is connected to top side of the humidifier body and is spaced apart from a bottom side of the humidifier body.

7. The humidifier of claim 1, wherein the humidifier body comprises a base portion and a cover portion.

8. The humidifier of claim 7, wherein the base portion and the cover portion are permanently bonded together.

9. The humidifier of claim 7, wherein the cover portion is removable from the base portion.

10. The humidifier of claim 7, wherein the base portion and the cover portion are provided with a tongue and a corresponding groove.

* * * * *